United States Patent [19]

Chandrasekaran et al.

[11] Patent Number: 5,188,826
[45] Date of Patent: Feb. 23, 1993

[54] TOPICAL OPHTHALMIC SUSPENSIONS

[75] Inventors: Santosh K. Chandrasekaran, Moraga; Margaret J. Reents, Alameda, both of Calif.; John C. Babcock, Olga, Wash.; Lyle M. Bowman, Pleasanton; Roy D. Archibald, Fremont, both of Calif.; Joseph R. Robinson, Madison, Wis.

[73] Assignee: InSite Vision Incorporated, Alameda, Calif.

[21] Appl. No.: 549,093

[22] Filed: Jul. 6, 1990

Related U.S. Application Data

[63] Continuation-in-part of Ser. No. 544,518, Jun. 27, 1990, abandoned, which is a continuation-in-part of Ser. No. 537,005, Jun. 12, 1990, abandoned, which is a continuation of Ser. No. 301,114, Jan. 25, 1989, abandoned, which is a continuation-in-part of Ser. No. 153,762, Feb. 8, 1988, abandoned, and a continuation-in-part of Ser. No. 429,770, Oct. 31, 1989, abandoned.

[51] Int. Cl.$^5$ .................. A61K 9/08; A01N 25/02
[52] U.S. Cl. .................. 424/78.04; 424/427; 424/428; 424/484; 424/486; 424/487; 514/772.3; 514/772.4; 514/772.6; 514/912; 514/913; 514/914; 514/944; 514/953; 514/954; 514/955
[58] Field of Search .............. 424/78, 427, 428, 443, 424/456, 486, 484, 487, 78.04, 772.3, 772.4, 772.6; 514/724, 912, 913, 914, 915, 944, 953, 954, 955

[56] References Cited

U.S. PATENT DOCUMENTS

| | | | |
|---|---|---|---|
| 3,947,573 | 3/1976 | Rankin | 514/397 |
| 4,271,143 | 6/1981 | Schoenwald et al. | 514/9 |
| 4,407,792 | 10/1983 | Schoenwald et al. | 514/397 |
| 4,474,751 | 10/1984 | Haslam et al. | 424/78 |
| 4,478,818 | 10/1984 | Shell et al. | 514/171 |
| 4,615,697 | 10/1986 | Robinson | 424/428 |
| 4,820,737 | 4/1989 | Schoenwald et al. | 514/654 |
| 4,911,920 | 3/1990 | Jani et al. | 424/78.04 |

FOREIGN PATENT DOCUMENTS

| | | |
|---|---|---|
| WO84/04680 | 5/1983 | PCT Int'l Appl. . |
| WO84/04681 | 5/1983 | PCT Int'l Appl. . |
| WO89/06964 | 2/1989 | PCT Int'l Appl. . |
| 2012634 | 2/1990 | Spain . |
| 2007091 | 5/1979 | United Kingdom . |
| 2013084 | 8/1979 | United Kingdom . |

OTHER PUBLICATIONS

Canadian Journal of Pharmaceutical Science, vol. 10, No. 1, pp. 16 et seq. (1975).
Pharmaceutica Acta Helvetiae, vol. 39, pp. 615 et seq. (1964).
Ophthalmology, 91, No. 10 (Oct. 1984), pp. 1199–1204 (Liebowitz et al.)
Klin. Mbl. Augenheilk., 189 (1986), at pp. 51–54 and pp. 254–257 (Marguardt et al.).
Pharmaceutica Acta Helvetiae, vol. 39, pp. 546 et seq. (1964).

Primary Examiner—Thurman K. Page
Assistant Examiner—Carlos Azpuru
Attorney, Agent, or Firm—Freed, Kjeldgaard, Griffin & Inskeep

[57] ABSTRACT

A topical, aqueous ophthalmic gel suspension for dry eye is administrable to the eye in drop form, remains as a gel in the eye for a prolonged time, and releases water and one or more ophthalmic demulcents or vasoconstrictors. It comprises water and from 0.1% to 6.5% by weight of lightly cross-linked carboxyl-containing polymer having a particle size of not more than about 50 μm in equivalent spherical diameter. The suspension is at a pH of from 6.6 to 8.0, has an osmolality of from 50 to 400 mOsM, and a viscosity of from about 500 to about 4,000 centipoise (0.5 to 4 Pa.s).

29 Claims, No Drawings

TOPICAL OPHTHALMIC SUSPENSIONS

REFERENCE TO RELATED APPLICATION

This application is a continuation-in-part of application Ser. No. 544,518 now abandoned which was filed on June 27, 1990 as a continuation-in-part of application Ser. No. 07/537,005, now abandoned, filed June 12, 1990, which was a file wrapper continuation of application Ser. No. 301,114, now abandoned, filed Jan. 25, 1989, which was a continuation-in-part of application Ser. No. 153,762, now abandoned filed Feb. 8, 1988. This application is also a continuation-in-part of application Ser. No. 429,770, now abandoned filed Dec. 31, 1989, whose disclosure is incorporated by reference to the full extent that it relates to ophthalmic preparations and applications.

FIELD OF THE INVENTION

This invention relates to new topical ophthalmic polymeric suspensions for easy administration to the eye in drop form, by or to a patient, with comfort and sustained efficacy to relieve minor irritation and redness of the eye, and to methods of preparing them. More particularly, this invention relates to new topical ophthalmic suspensions, for dry eye applications, comprising aqueous suspensions of particular lightly cross-linked polymers of acrylic acid or the like, which suspensions also contain one or more ophthalmic demulcents (ophthalmic lubricating agents), one or more ophthalmic vasoconstrictors, or combinations of these two components.

BACKGROUND OF THE INVENTION

Several specific ophthalmic conditions are known colloquially and collectively as "dry eye." These conditions are more properly termed "tear deficiencies" or "tear film abnormalities" [Michael Lemp, Ch. 14 "Diagnosis and Treatment of Tear Deficiencies" in Duane and Jaeger's "Clinical Ophthalmology" (New York: Harper & Row, 1980)].

When the tear deficiency is largely due to a decrease in the aqueous component of the lacrimal fluid, as opposed to the outer lipid or inner mucin components, it is known as keratoconjunctivitis sicca (KCS). When KCS is associated with systemic problems, the condition is often referred to as Sjogren Syndrome. There are many other causes of dry eye, however, among which are severe inflammation, alkali burn, and the like.

There are also dry eye syndromes associated with aging, with prolonged use of contact lenses, or with environmental extremes, in which rapid tearfilm loss through evaporation becomes increasingly severe with increasing heat, wind velocity, exposure to tobacco smoke and other wind-borne particulate matter, etc.

The terms "dry eye applications," "relief of minor irritation" and "relief of redness of the eye" are used herein in their broadest sense.

Medicaments have been administered to the eye in eyedrops, ointments or creams, in gelatin lamellae or other biologically soluble or insoluble films or sheets, by dispensing ocular inserts, and as suspensions or emulsions in aqueous and non-aqueous vehicles. Certain of these dosage forms have also been used to administer ophthalmic formulations for the relief of dry eye or redness of the eye due to minor eye irritations. The disadvantages associated with many of these ophthalmic medicament delivery systems are well known. Conventional eyedrops in the form of aqueous solutions or suspensions are rapidly washed away by the eye's tear fluid or drain spontaneously away through the nasalacrimal duct. Ointments or creams blur the vision, and also have comparatively short residence times in the eye. Gelatin lamellae or other films or sheets, ocular inserts and non-aqueous suspensions and emulsions all can cause immediate pain and continuing discomfort and can also interfere with vision.

Highly viscous aqueous gels formed from carboxy vinyl polymers, such as those disclosed (but not even as dry eye formulations) in Schoenwald et al. U.S. Pat. Nos. 4,271,143 and 4,407,792, issued June 2, 1981 and Oct. 4, 1983, respectively, are difficult to administer so as to provide consistent, accurate dosages and may be uncomfortable to administer as well. Indeed, above a viscosity of about 30,000 cps, reliable administration in drop form is at best difficult to achieve and at worst impossible.

Schoenwald et al. U.S. Pat. No. 4,820,737, issued Apr. 11, 1989, discloses tear stimulant compositions of a much lower viscosity, i.e., from about 4 to 100 cps, containing, for example, N-cyclohexyl-N-methyl-2-phenylethylamine and an ophthalmically acceptable carrier which can include a viscolyzer such as hydroxyethylcellulose, hydroxypropyl methylcellulose, methylcellulose or a polyacrylamide.

UK Patent Application No. GB 2007091A (Toko) describes ophthalmic drug-containing, carboxy vinyl polymer based gels, cross-linked with a polyalkenyl polyether, over a wider viscosity range, namely 1,000 to 100,000 cps. Tear replenishment is among the contemplated uses. The relatively low viscosity preparations having viscosities of 1,000 to 10,000 are stated to have good flowability and to be amenable to application by drops directly into the mucous membrane around the eyeball. However, the use of sodium chloride in the preparation is recommended in Toko for sustained efficiency because sodium chloride is said to delay breakdown of the gel when the compositions are applied to the mucous membrane of the eye. But, the sodium chloride is also said to convert the gel to a liquid with a great reduction in viscosity. Therefore, when sodium chloride is added to the composition, increased polymer amounts are recommended to compensate for such viscosity reduction due to the addition of sodium chloride.

Robinson, U.S. Pat. No. 4,615,697, issued Oct. 7, 1986, discloses a controlled release treatment based on a bioadhesive which is described as a water-swellable, although water insoluble, fibrous, cross-linked carboxyfunctional polymer with a plurality of repeating units in which about at least 80 percent thereof contain at least one carboxy functionality and a crosslinking agent (0.05 to 1.5 percent) that is substantially free of polyalkenyl polyether. It is noteworthy that whereas Robinson seeks to exclude the use of polyalkanyl polyether crosslinkers (as are present in Carbapol 934), Toko finds Carbapol 934 especially useful. Robinson discloses the use of a polymer sized to pass through a 100 mesh sieve screen with fluorometholone; but it does not disclose or teach use as a moisturizing agent in a dry eye formulation, particularly as set forth hereafter.

An article by Liebowitz et al. in Ophthalmology, 91, No. 10 (October 1984), pp. 1199-1204, reports on experiments on treating dry eye conditions with a high viscosity gel material said to be: "a clear, semisolid formulation of synthetic, high molecular weight, cross-linked polymers of acrylic acid"; p. 1199; obtained from Alcon Laboratories, Inc., the assignee of the Schoenwald et al. patents. The other constituents of this gel, if any, are not identified, although a commentator whose remarks accompany the article speculates that water could be present; p. 1204.

Several polymeric dry eye formulations, including the commercially available Vidisic ® gel dry eye formulation (Dr. Mann Pharma, Berlin, Germany) are described in two articles by Marquardt and Marquardt et al. that appeared in Klin. Mbl. Augenheilk., 189 (1986) at pp. 51-54 and 254-257, respectively. Vidisic ® gel contains polyacrylic acid, MW about 4 million, physiological salt solution, sorbitol and a preservative. Other dry eye formulations described in these articles, which did not contain acrylic acid polymers, were said to contain methylcellulose and its derivatives, e.g., hydroxyethylcellulose, or polyvinyl alcohol and polyvinylpyrrolidone.

Although some of the foregoing ophthalmic formulations can be acceptable for some purposes in connection with the control of dry eye, they can be unacceptable for other purposes. For example, problems of ease and reliability of administration, comfort and/or sustained efficacy can be encountered. Also, in formulations based on prescription drugs, ease of access can present a problem.

OBJECTS AND SUMMARY OF PREFERRED FORMS OF THE INVENTION

It is an object of this invention to provide new topical ophthalmic suspensions for dry eye applications, and for relief of minor irritation and redness of the eye, which obviate or minimize problems of the sort previously mentioned.

It is a particular object of this invention to provide such new topical ophthalmic suspensions that are easily administrable to the eye in drop form.

A further object of this invention is to provide such new topical ophthalmic suspensions that are easily administrable in drop form that comprise aqueous suspensions of particular lightly cross-linked polymers of acrylic acid or the like containing an ophthalmic demulcent.

Another object of this invention is to provide such new topical ophthalmic suspensions that are easily administrable in drop form and, after coming into contact with the eye's tear fluid, remain as a gel in the eye for a prolonged period of time.

Yet another object of this invention is to provide such new topical ophthalmic suspensions that are easily administrable in drop form, are comfortable in the eye and have an appreciable duration of action.

A still further object of this invention is to provide methods of preparing the new topical ophthalmic suspensions.

An additional object of this invention is to provide a method of administering and treating dry eye conditions with the new topical ophthalmic suspensions.

In accordance with the present invention lightly cross-linked carboxyl-containing polymers made up of predominantly carboxyl-containing monomers, prepared by suspension or emulsion polymerizing acrylic acid or the like and a non-polyalkenyl polyether difunctional cross-linking agent such as divinyl glycol (3,4-dihydroxy-1,5-hexadiene) or the like to an average dry particle size of not more than about 50 μm in equivalent spherical diameter, e.g., Carbopol 976 carboxyl-containing polymer, are formulated with one or more ophthalmic demulcents or ophthalmic vasoconstrictors, or both, and, optionally one or more ophthalmic adjuvants and, if desired, a preservative, into gel suspensions in aqueous medium in which the amount of polymer, the pH, and the osmolality are within the ranges given hereinbelow. Such suspensions provide topical ophthalmic formulations for use as artificial tear supplements, for dry eye applications, and for relief of minor irritation and redness of the eye. They have suitably low viscosities that permit them to be easily administered to the eye, in drop form, in consistent, accurate dosages. These suspensions, which may be introduced into the precorneal pockets of the eyes, remain as a gel in the eye in contact with the conjuntival mucosa for a time period sufficient to moisturize that contacted mucous membrane. Indeed, the contact lasts over prolonged periods of time to provide comfortable and sustained release of both water and the ophthalmic demulcent(s) or vasoconstrictor(s) present.

The carboxyl-containing polymer system is itself hydrophilic in nature. The demulcents themselves constitute another polymeric system which is hydrophilic in nature. The introduction of a second hydrophilic component (here, the demulcent) could readily break up the matrix of the first hydrophilic system (the carboxyl-containing polymer system). Not only could such an additive adversely interfere with the interaction that is necessary to produce desired gelation, but also it could cause the polymer of the first system to precipitate out of suspension. In the present case, however, it has been found that the demulcents can be and are added to the basic polymer system to yield a homogeneous suspension that provides an effective and sustained release dry eye formulation.

About 0.025 to about 1.0 mg of the polymer in the basic system per square centimeter of the contacted mucosa of the eye is a desired application for comfort. This would be about 25 to about 50 microliters of a composition containing about 0.2 to about 3 weight percent of that polymer.

Once they have been dropped into the eye, the formulations of the present invention remain as gels in the eye for prolonged periods of time. During such prolonged periods the gelled suspensions serve to protect, lubricate and moisten the eye's mucous membrane surfaces, to relieve redness of the eye caused by minor irritation, or both. They do so by slowly releasing both the demulcent and the water entrapped therein to relieve conjunctival dryness and irritation resulting from a disruption or deficiency of the lacrimal system in which too little tear fluid is produced, the tear fluid evaporates too rapidly, or an abnormality exists in the composition of the tears or with distribution of tears on the eye's surface, or by slowly releasing the vasoconstrictor, if present.

Those of the formulations of this invention suitable for non-prescription or over-the-counter sale will be used:

for the temporary relief of burning and irritation due to dryness of the eye;

for the temporary relief of discomfort due to minor irritations of the eye, or to exposure to wind or sun;

as a protectant against further irritation or to relieve dryness of the eye; and to relieve redness of the eye due to minor eye irritations.

The topical, prescription drug-free, aqueous ophthalmic gel suspensions comprise water, and from about 0.1% to about 6.5% by weight, preferably from about 0.1% to about 2.0% by weight, based on the total weight of the suspension, of the lightly cross-linked carboxyl-containing polymer having a particle size preferably of not more than about 30 μm, more preferably not more than about 20 μm, and still more preferably from about 1 or about 2 to about 5 μm, in equivalent spherical diameter, at least about 60% by weight, and preferably substantially all, of the polymer having been prepared by suspension or emulsion polymerizing at least about 50%, more preferably at least about 90%, by weight of one or more carboxyl-containing monoethylenically unsaturated monomers and from about 0.01% to about 5% by weight of the non-polyalkenyl polyether difunctional cross-linking agent, preferably 3,4-dihydroxyhexa-1,5-diene in an amount of from about 0.01% to about 1% by weight, the weight percentages of monomers being based on the total weight of monomers polymerized, and from about 0.01% to about 4% by weight, based on the total weight of the suspension, of at least one ophthalmic demulcent, or from about 0.01% to about 0.2% by weight, based on the total weight of the suspension, of at least one ophthalmic vasoconstrictor, or a mixture of at least one ophthalmic demulcent and at least one ophthalmic vasoconstrictor from within the above-stated ranges. The suspensions are at a pH of from about 6.6 to about 8.0, preferably from about 6.8 to about 7.6 and more preferably from about 7.2 to about 7.4, and an osmolality of from about 50 to about 400 mOsM, preferably from about 100 to about 300 mOsM. The osmolality is preferably achieved using a physiologically and ophthalmologically acceptable salt, most preferably sodium chloride, in an amount of from about 0.01% to about 1% by weight, based on the total weight of the suspension. The viscosity is from about 500 to about 4,000 centipoise, preferably about 600 to about 3000 cps, as measured at about 25° C. using a Brookfield Digital LVT Viscometer equipped with a number 31 spindle and a 13R small sample adapter at 12 rpm.

It is preferred that the ophthalmic demulcent be at least one of sodium carboxymethyl-cellulose, hydroxyethylcellulose, hydroxypropylmethylcellulose, methylcellulose, dextran 70, gelatin, glycerin, polyethylene glycol 300, polyethylene glycol 400, polysorbate 80, propylene glycol, polyvinyl alcohol or polyvinylpyrrolidone. Gelatin, or mixtures of gelatin and hydroxyethylcellulose or dextran or mixtures of dextran and polyethylene glycol, are particularly preferred. It is also preferred that the ophthalmic vasoconstrictor be at least one of ephedrine hydrochloride, naphazoline hydrochloride, phenylephrine hydrochloride or tetrahydrozoline hydrochloride.

The suspension desirably also contains from about 0.01 to about 0.5% by weight, based on the total weight of the suspension, of a stabilizer. The preferred stabilizer is ethylenediaminetetraacetic acid or its sodium salt, present in an amount of from about 0.025 to about 0.3% by weight, based on the total weight of the suspension.

In the most preferred forms of the invention, the particles are not only subject to the upper size limits described above, but also to a narrow particle size distribution so as to be essentially monodisperse. Such use of a monodispersion of particles, which aids in good particle packing, also maximizes residence time and yields particularly desirable sustained efficacy.

At least about 80%, more preferably at least about 90% and most preferably at least about 95%, of the At least about 80%, more preferably at least about 90% and most preferably at least about 95%, of the particles should be within a no more than about 10 μm band of major particle size distribution, and overall (i.e., considering particles both within and outside such band) there should be no more than about 20%, preferably no more than about 10% and most preferably no more than about 5% fines (i.e., particles of a size below 1 μm). It is also preferred that as the average particle size is lowered from the upper limit of 50 μm, to lower sizes such as 6 μm, that the band of major particle size distribution be also narrowed, for example to 5 μm. A range of from about 1 to about 5 μm is most preferred.

The foregoing and other aspects, objects and advantages of the present invention, as well as its nature, scope and utilization, will become more apparent to those skilled in the art from the following detailed description and the appended claims.

DETAILED DESCRIPTION OF THE INVENTION

The lightly cross-linked polymers of acrylic acid or the like used in practicing this invention are, in general, well known in the art. In preferred embodiments such polymers are ones prepared from at least about 90%, and preferably from about 95% to about 99.9% by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers are cross-linked by using a small percentage, i.e., from about 0.01% to about 5%, and preferably from about 0.1% to about 1%, based on the total weight of monomers present, of a non-polyalkenyl polyether difunctional cross-linking monomer such as 3,4-dihydroxyhexa-1,5-diene (divinyl glycol); 2,5-dimethyl-1,5-hexadiene; divinylbenzene; N,N-diallylacrylamide; N,N-diallylmethacrylamide, or the like.

The lightly cross-linked polymers can of course be made from a carboxyl-containing monomer or monomers as the sole monoethylenically unsaturated monomer present, together with the cross-linking agent or agents. They can also be polymers in which up to about 40%, and preferably from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethyl-hexylacrylate, octyl methacrylate, 2-hydroxyethylmethacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers. Particularly preferred polymers are lightly cross-linked acrylic acid polymers wherein the cross-linking monomer is 3,4-dihydroxyhexa-1,5-diene or 2,5-dimethylhexa-1,5-diene, e.g., Carbopol 976, a carboxyl-containing polymer prepared by suspension polymerizing acrylic acid and divinyl glycol and having an average dry particle size of about 5 $\mu$m.

The lightly cross-linked polymers used in practicing this invention are preferably prepared by suspension or emulsion polymerizing the monomers, using conventional free radical polymerization catalysts, to a dry particle size such that, after sieving and mixing if necessary or desirable, at least about 80%, more preferably at least about 90% and most preferably at least about 95%, of the dry polymer particles are within a no more than about 10 $\mu$m band of major particle size distribution which has an upper limit of 30 $\mu$m, more preferably 20 $\mu$m, in equivalent spherical diameter. No more than 20% preferably no more than 10%, and most preferably no more than about 5% of the above particles are fines. In general, such polymers will range in molecular weight estimated to be about 250,000 to about 4,000,000, and preferably from about 500,000 to about 2,000,000.

Aqueous suspensions formulated in accordance with this invention containing polymer particles prepared by suspension or emulsion polymerization whose dry particle size is appreciably larger than about 30 $\mu$m in equivalent spherical diameter are less comfortable when administered to the eye than suspensions otherwise identical in composition containing polymer particles whose equivalent spherical diameters are, on the average, no larger than about 30 $\mu$m. It has been discovered, furthermore, that lightly cross-linked polymers of acrylic acid or the like prepared to a dry particle size appreciably larger than about 30 $\mu$m in equivalent spherical diameter and then reduced in size, e.g., by mechanically milling or grinding, to a dry particle size of not more than about 30 $\mu$m in equivalent spherical diameter do not work as well as polymers made to size specifically from aqueous suspensions as taught by this invention.

While we do not wish to be bound by any theory or mechanism advanced to explain the functioning of this invention, one possible explanation for the differences noted when such mechanically milled or ground polymer particles are the sole particulate polymer present is that grinding disrupts the spatial geometry or configuration of the larger than 30 $\mu$m lightly cross-linked polymer particles, perhaps by removing uncross-linked branches from polymer chains, by producing particles having sharp edges or protrusions, or by producing ordinarily too broad a range of particle sizes to afford satisfactory delivery system performance.

In any event, such mechanically reduced particles are less easily hydratable in aqueous suspension than particles prepared to the appropriate size by suspension or emulsion polymerization, and suspensions made from them alone are less able to be sustained as a gel in the eye under the influence of tear fluid, and are less comfortable, than gels produced using the aqueous suspensions of this invention. However, up to about 40% by weight, e.g., from about 0% to over 20% by weight, based on the total weight of lightly cross-linked particles present, of such milled or ground polymer particles having equivalent spherical diameters of not more than about 30 $\mu$m can be admixed with solution or emulsion polymerized polymer particles also having dry particle diameters of not more than about 50 $\mu$m when practicing this invention. Such mixtures will also provide satisfactory viscosity levels in the ophthalmic suspensions for dry eye applications of this invention, coupled with ease and comfort of administration and satisfactory sustained release of the ophthalmic demulcent to the eye, particularly when such milled or ground polymer particles, in dry form, average from about 1.0 to about 5 $\mu$m or about 6 $\mu$m in equivalent spherical diameter.

Ophthalmic demulcents are agents, usually water soluble polymers, applied topically to the eye to protect and lubricate mucous membrane surfaces and relieve dryness and irritation. Ophthalmic demulcents or lubricating agents that can be used in practicing invention include one or more of those set out in Table I below. The amount of ophthalmic demulcent(s) used will generally range from about 0.01% to about 4% by weight, based on the total weight of the formulation, and when the demulcent is one of those set out in, for example, 21 CFR §394,12, it will be used in an amount within the range given for it there:

TABLE I

| Ophthalmic Demulcent | Amount[1] |
| --- | --- |
| (a) Cellulose derivatives: | |
| (1) Carboxymethylcellulose sodium | 0.2–2.5% |
| (2) Hydroxyethylcellulose | 0.2–2.5% |
| (3) Hydroxypropylmethylcellulose | 0.2–2.5% |
| (4) Methylcellulose | 0.2–2.5% |
| (b) Dextran 70 | 0.1%[2] |
| (c) Gelatin | 0.01% |
| (d) Polyols, liquid: | |
| (1) Glycerin | 0.2–1% |
| (2) Polyethyleneglycol 300 | 0.2–1% |
| (3) Polyethyleneglycol 400 | 0.2–1% |
| (4) Polysorbate 80 | 0.2–1% |
| (5) Propyleneglycol | 0.2–1% |
| (e) Polyvinyl alcohol | 0.1–4% |
| (f) Povidone[3] | 0.1–2% |

[1]Percents are by weight, based on total weight of formulation
[2]When used with another polymeric demulcent listed in 37 CFR §349.12
[3]Polyvinylpyrrolidone.

In general, the ophthalmic demulcent or demulcents employed in formulations coming within this invention (mixtures of up to three of the above-listed demulcents have been used in developing formulations embodying this invention) will be used in any amounts from within the above-recited ranges that are compatible with the lightly cross-linked carboxyl-containing polymer. Compatibility in this context means:

freedom from the separation of the components of the formulation, whether upon formulation or in storage;

the ability of the demulcent-containing gel to be sustained in the presence of tear fluid in the eye for acceptably long residence times; and the ability to introduce the demulcent-containing gel into the eye without provoking more than transient blurring of vision or initial stinging that normally accompanies placing virtually any foreign material in the eye.

Ophthalmic vasoconstrictors are pharmacologic agents which, when applied topically to the mucous membranes of the eye, cause temporary constriction of the conjunctival blood vessels. They are used to relieve redness of the eye caused by minor irritation. Ophthalmic vasoconstrictors that can, if desired, also be used in practicing this invention, alone or together with one or more ophthalmic demulcents, include one or more of those set out in, for example, 21 CFR §349.18, in an amount generally ranging from about 0.01% to about 0.2% by weight, based on the total weight of the formulation, and preferably in the amounts also set out in that portion of the FDA's OTC drug monograph:

TABLE II

| Ophthalmic Vasoconstrictor | Amount[1] |
|---|---|
| (a) Ephedrine hydrochloride | 0.123% |
| (b) Naphazoline hydrochloride | 0.01–0.03% |
| (c) Phenylephrine hydrochloride | 0.08–0.2% |
| (d) Tetrahydrozoline hydrochloride | 0.01–0.05% |

[1]Percents by weight, based on total weight of formulation.

Ophthalmic adjuvants that can, if desired, also be included with the ophthalmic demulcent(s), ophthalmic vasoconstrictor(s), or both when practicing this invention include ethylenediaminetetraacetic acid or its sodium salt (sodium EDTA or sodium edetate), used as stabilizers of the polymer, which can be present in amounts ranging from about 0.01 to about 0.5% by weight, and preferably from about 0.025 to about 0.3% by weight, based on the total weight of the formulation, sorbitol and like polyols, which can be present in amounts ranging up to about 6.0% by weight, based on the total weight of the formulation, and the like.

The aqueous suspensions of this invention will contain amounts of lightly cross-linked polymer particles sufficient to give gels stable enough to have prolonged residence time in the eye and yet not cause more than a transient blurring of vision. Preferably, the polymer content of the suspension will range from about 0.1% to about 6.5% by weight, and most preferably from about 0.5% to about 1.3% by weight, based on the total weight of the aqueous suspension. When using Carbopol 976 carboxyl-containing polymer, for example, amounts ranging from about 0.1% to about 2.0% by weight, and preferably from about 0.6 to about 0.8% by weight, will be used, these amounts again being based on the total weight of the aqueous suspension.

These aqueous suspensions will preferably be prepared using USP purified water, or equivalent, having no physiologically or ophthalmologically harmful constituents, and will be adjusted to a pH about 6.5, e.g., a pH of from about 6.6 to about 8.0, preferably from about 6.8 to about 7.6, and most preferably from about 7.2 to about 7.4, using physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like, and salts and buffers such as citrate/dextrose, sodium bicarbonate, ammonium chloride, and mixtures of the aforementioned acids and bases.

When formulating the aqueous suspensions of this invention, their osmolality ($\pi$) will be adjusted to from about 50 milliosmolar (mOsM) to about 400 mOsM, and preferably from about 100 to about 300 mOsM, using appropriate amounts of physiologically and ophthalmologically acceptable salts. Sodium chloride is preferred to approximate physiologic fluid, and amounts of sodium chloride ranging from about 0.01% to about 1% by weight, preferably from about 0.3% to about 0.7% by weight, and most preferably about 0.6%, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like, can also be used in addition to or instead of sodium chloride to achieve osmolalities within the above-stated ranges.

The amounts of lightly cross-linked polymer particles, the pH, and the osmotic pressure chosen from within the above-stated ranges will be correlated to give aqueous suspensions having viscosities ranging from about 500 to about 4,000 centipoise, and preferably from about 600 to about 3,000 centipoise, as measured at room temperature (about 25° C.) using a Brookfield Digital LVT Viscometer equipped with a number 31 spindle and a 13R small sample adapter at 12 rpm. Such suspensions provide gels which remain as gels in the eye for prolonged periods of time, e.g., for at least about 1 hour, and preferably at least about 2 hours, more preferably at least about 4 hours, depending on patient variability. The actual residence times of such gels in the eye can be determined, for example, by staining with fluorescein at various times and observing the decline in fluorescence of the residual gel with the aid of a slit lamp.

Particularly preferred aqueous dry eye formulations coming within the scope of this invention include the following:

TABLE III

| | Polymer[1,2] | EDTA[3] | Sodium Chloride | Demulcents |
|---|---|---|---|---|
| A | 0.7% | 0.1% | 0.6% | 0.1% dextran 70 and 0.01% gelatin |
| B | 0.7% | 0.1% | 0.6% | 0.2% hydroxyethyl-cellulose and 0.01% gelatin |
| C | 0.6% | 0.1% | 0.6% | 0.1% dextran 70 and 0.2% polyethylene glycol 400 |

[1]All percentages are by weight, based on the total weight of the formulation.
[2]Carbopol 976 carboxyl-containing polymer.
[3]Stabilizer, added as the sodium salt.

The pH of these formulations is 7.2–7.4, their osmolality is about 250 mOsM, and their viscosities are: A=1520 cps, B=1430 cps, C=646 cps, all measured at about 25° C. using a Brookfield Digital LVT Viscometer equipped with a number 31 spindle and a 13R small sample adapter at 12 rpm.

The gels of this invention have residence times in the eye ranging from about 0.5 to about 6 hours, e.g., from about 1 to about 4 hours. The water, ophthalmic demulcent(s) and/or vasoconstrictor(s) contained in the aqueous suspension as administered will be released from the gel at rates that depend on such factors as the demulcent or vasoconstrictor itself and its physical form, the extent of demulcent or vasoconstrictor loading and the pH of the system, as well as on any ophthalmic adjuvants and preservatives which may also be present.

The topical ophthalmic aqueous suspensions for dry eye applications of this invention can be formulated in any of several ways. For example the demulcent(s), with or without a vasoconstrictor, or a vasoconstrictor itself without demulcent(s), the lightly cross-linked polymer particles, the osmolality-adjusting salt and any of the optional ingredients also being used can be pre-blended, added to all or part of the water, and stirred vigorously until apparent polymer dispersion is complete, as evidenced by the absence of visible polymer aggregates, which usually occurs within about an hour. Sufficient pH adjusting agent is then added incrementally to reach the desired pH, and more water to reach 100 percent formula weight can be added at this time, if necessary. Another convenient method involves dissolving the demulcent(s) or vasoconstrictor(s) in about 90 percent of the final water volume with stirring. The lightly cross-linked polymer particles and the osmolality-adjusting salt may first be blended in dry form and added to the demulcent or vasoconstrictor solution and stirred until apparent polymer hydration is complete. Any optional ingredients can then be added. Following the incremental addition of sufficient pH adjusting agent to reach the desired pH, the remainder of the water is added, with stirring, to bring the suspension to 100 percent formula weight.

A preferred method of formulating the topical ophthalmic suspensions of this invention involves adding the polymer to 90 grams of water per 100 grams of gel, then stirring for about 1 hour until the gel is fully hydrated. One or more demulcents, and vasoconstrictor(s) if one or more of such substances are to be employed with the demulcent(s), or vasoconstrictor(s) with demulcent(s), ar then added as aqueous solutions, with stirring. Next, sodium edetate and sodium chloride are added as solids, together with sufficient water to bring the mass to 100 grams, and the pH is adjusted to the final pH, e.g., with 10N sodium hydroxide.

The thus-prepared aqueous suspensions are sterilized, preferably by briefly heating, e.g., for about 30 minutes with steam at about 121° C., and then filled into appropriate containers. Preservative-free suspensions may be filled into unit-dose containers, at the preferred viscosity, eliminating the potential for preservative-related irritation and sensitization of the corneal epithelium, as has been observed to occur particularly from ophthalmic medicaments containing preservatives such as, for example, mercurial preservatives.

Suspensions containing preservatives may also be filled into multiple-dose containers at the preferred viscosity, if desired, particularly since the viscosities of the aqueous suspensions of this invention permit constant, accurate dosages to be administered dropwise to the eye as many times each day as necessary. In those suspensions where preservatives are to be included, suitable preservatives include benzalkonium chloride in amounts ranging from about 1.0025 to about 0.01%, chlorobutanol, preferably 0.5%, chlorobutanol chloral derivative, preferably 0.5%, methyl paraben and propyl paraben, preferably about 0.01 to about 0.05%, sorbic acid, preferably about 0.01%, Cetrimide, preferably about 0.01%, polyquat, preferably about 0.001%, cetyl bromide, preferably about 0.01%, and the like, each of the foregoing preservative amounts being based on the total weight of the formulation.

In order that those skilled in the art can more fully understand this invention, the following examples are set forth. These examples are given solely for purposes of illustration, and should not be considered as expressing limitations unless so set forth in the appended claims. All parts and percentages are by weight unless otherwise stated.

PREPARATION A

A demulcent-free dry eye/tear substitute formulation was prepared by adding 0.8% Carbopol 976 carboxyl-containing polymer having a dry particle size of 5μm to 97% of purified water in a vessel and stirring at high speed for approximately 15 minutes. Sodium chloride, 0.6%, was then added to the aqueous polymer suspension with stirring.

The resulting suspension was steam sterilized at 121° C. for 45 minutes. The suspensions was then cooled to about 50° C. Next 10 N sodium hydroxide solution was sterile filtered into the suspension with stirring to adjust the pH to 7.4. Additional purified water was then sterile filtered into the suspension with stirring to bring the final formulation percentage to 100%. The final aqueous suspensions had an osmolality of approximately 270 mOsM, a viscosity of approximately 3600 cps, measured as above, and a pH of about 7.4.

PREPARATION B

The procedure of Preparation A was repeated in every respect but one, namely, 0.7% of Carbopol 976 carboxyl-containing polymer was used. The final aqueous suspension had an osmolality of approximately 232 mOsM, a viscosity of approximately 1850 cps, measured as above, and a pH of about 7.55.

EXAMPLE I

A dry eye formulation containing 0.8% polymer and 0.01% gelatin was prepared by first adding 0.8 part of Carbopol 976 carboxyl-containing polymer having a dry particle size of 5 μm to 90 parts of purified water and mechanically stirring at approximately 400 rpm for 1 hour to form a polymer suspension.

One part of a solution prepared by adding 1 part of gelatin USP to 99 parts of purified water, with heating to 90° C., was added to the above-prepared polymer suspension, and the resulting mixture was stirred for 15 minutes, following which 0.1 part of solid sodium edetate and 0.6 part of sodium chloride were added, also with stirring. Water was then added in an amount sufficient to give 100 parts of suspension, with stirring then being continued for a further 10 minutes. Next, the pH of the suspension was adjusted to 7.4 by adding sufficient 10N aqueous sodium hydroxide and, after stirring for an additional 15 minutes, the formulation was steam sterilized at 121° C. for 30 minutes, then poured into sterile, unit-dose containers.

EXAMPLE II

The procedure of Example I above was repeated in every detail except for the following. 0.7 Part of Carbopol 976 carboxyl-containing polymer was used to prepare the initial suspension, which was then admixed with 0.5 part of a solution prepared by adding 40 parts of polyethylene glycol 400 to 60 parts of purified water, instead of the gelatin solution.

EXAMPLE III

The procedure of Example I above was again repeated in every detail except for the following. 0.7 part of Carbopol 976 carboxyl-containing polymer was used to prepare the initial suspension, which was then admixed with (1) 0.5 part of a solution prepared by adding 40 parts of polyethylene glycol 400 to 60 parts of purified water and (2) one part of a solution prepared by adding 10 parts of dextran 70 to 90 parts of purified water, instead of the gelatin solution.

EXAMPLE IV

The procedure of Example III above was repeated in every detail but one, namely, one part of the gelatin solution of Example I was used in place of the polyethylene glycol 400 solution.

EXAMPLE V

The procedure of Example III above was again repeated in very detail but one, namely, 0.6 part of Carbopol 976 carboxyl-containing polymer was used to prepare the initial suspension.

EXAMPLE VI

The procedure of Example II above was repeated in every detail but one, namely, 0.5 part of a solution prepared by adding five parts of hydroxyethylcellulose to 95 parts of purified water was used instead of the polyethylene glycol 400 solution.

EXAMPLE VII

The procedure of Example VI above was repeated in every detail but one, namely, one part of the gelatin solution of Example I was added to the initial suspension in addition to the hydroxyethylcellulose solution.

EXAMPLE VIII

The procedure of Example V above was repeated in every detail but one, namely, 4 parts of the hydroxyethylcellulose solution of Example VI was added to the initial suspension in place of the polyethylene glycol 400 solution.

EXAMPLE IX

The procedure of Example II above was repeated in every detail but one, namely, one part of the polyethylene glycol 400 solution, rather than 0.5 part, was used.

The demulcent-free formulation of Preparation A and the demulcent-containing formulations of Examples I, II, III, IV, VII and IX above were studied in single dose administration to the eyes of six volunteers in comparison with three commercially-available products:

Tears Naturale ® solution containing dextran 70, hydroxypropyl methylcellulose, 0.01% benzalkonium chloride and disodium edetate, in purified water; Alcon Laboratories, Inc.;

Tears Naturale II ® solution, containing 0.1% dextran 70, 0.3% hydroxypropyl methylcellulose 2910, 0.001% Polyquad polyquaternium-1 preservative, disodium edetate, potassium chloride and sodium chloride in purified water; Alcon Laboratories, Inc.; and Celluvisic ® solution, containing 1% sodium carboxymethylcellulose, calcium chloride, potassium chloride, sodium chloride and sodium lactate in purified water; Allergan Pharmaceuticals;

each of which was otherwise administered in accordance with the manufacturers' directions.

The study was a randomized, single blind study. Estimates of duration of moistness or lubricity were recorded as measures of efficacy. Estimates of duration of transient stinging and blurring were recorded as measures of comfort or side effect. The results obtained in this study are summarized in Table IV below. Based on these results, the compositions were then scored for duration of efficacy and for comfort and rated comparatively as shown in Table V below.

TABLE IV

| Formulation | Carboxyl-Containing Polymer, %[1] | Demulcent(s), % | Duration[2] of: | | |
|---|---|---|---|---|---|
| | | | Moistness | Blurring | Stinging |
| Preparation A | 0.8 | None | 132 | 16 | 2 |
| Example I | 0.8 | 0.01 gelatin | 143 | 35 | 7[3] |
| Example IX | 0.7 | 0.4 polyethyleneglycol 400 | 62 | 17 | 15[4] |
| Example II | 0.7 | 0.2 polyethyleneglycol 400 | 111 | 29 | 8[5] |
| Example III | 0.7 | 0.2 polyethyleneglycol 400 and 0.1 dextran 70 | 127 | 2 | 0[6] |
| Example VII | 0.7 | 0.2 hydroxyethylcellulose and 0.01 gelatin | 136 | 5 | 0.2[7] |
| Example IV | 0.7 | 0.1 dextran 70 and 0.01 gelatin | 134 | 3 | 0[8] |
| Tears Naturale ® Solution | — | hydroxypropyl methylcellulose and dextran 70 | 40 | 1 | 0.2 |
| Tears Naturale II ® Solution | — | hydroxypropyl methylcellulose and dextran 70 | 40 | 2 | 0.2 |
| Celluvisic ® Solution | — | sodium carboxymethylcellulose | 94 | 13 | 0 |

[1]Carbopol 976 polymer.
[2]In minutes.
[3]Adding gelatin as a demulcent (Example I) to Preparation A sustained Preparation A's duration of moistness but increased the duration of both blurring and stinging.
[4]Reducing Preparation A's amount of carboxyl-containing polymer (Example IX) and adding demulcent decreased Preparation A's duration of moistness, slightly increased its duration of blurring and increased its duration of stinging.
[5]Use of lesser amount of demulcent (Example II) than that employed in Example IX did not significantly decrease the latter formulation's duration of blurring and stinging.
[6]The addition of dextran 70 (Example III) to the formulation of Example II markedly reduced the latter's duration of stinging without materially affecting its duration of moistness; duration of blurring, however, was not improved.
[7]Slightly reducing Example I's amount of carboxyl-containing polymer and adding hydroxyethylcellulose as a second demulcent (Example VII) retained the former formulation's duration of moistness while minimizing the duration of blurring and stinging.
[8]Examples III and IV suggest that replacing some of the carboxyl-containing polymer of Example I with dextran (Example III), or using dextran instead of polyethylene glycol 400 as the demulcent (Example IV), retains Example I's formulation's duration of moistness while minimizing the duration of blurring and stinging.

TABLE V

| Formulation | Efficacy[1] | Comfort[2] |
|---|---|---|
| Preparation A | 1 | 2 |
| Example I | 1 | 3 |
| Example IX | 3 | 3 |
| Example II | 2 | 3 |
| Example III | 2 | 2 |
| Example VII | 1 | 1 |
| Example IV | 1 | 1 |
| Tears Naturale ® Solution | 4 | 1 |
| Tears Naturale II ® Solution | 4 | 1 |

TABLE V-continued

| Formulation | Efficacy[1] | Comfort[2] |
| --- | --- | --- |
| Celluvisic ® Solution | 3 | 2 |

[1] The impression of moistness and lubricity was judged to be a measure of efficacy, and was scored as follows:
1 = 120 minutes or longer.
2 = 100 to 120 minutes.
3 = 50 to 100 minutes.
4 = 20 to 50 minutes.

[2] The impression of overall comfort was scored based on the impression of transient stinging and transient blurring, as follows:
Stinging: after installation of the drops
1 = transient stinging did not occur, or faint transient stinging occurred but lasted for no more than 2 minutes.
2 = transient stinging was felt for more than 2 minutes.
Blurring:
1 = transient, minor blurring of vision occurred episodically, after installation of the drops, over the course of a few minutes.
2 = transient blurring occurred episodically over a period of 10 minutes or longer.
The combined comfort score was derived from the stinging and blurring scores so that the compositions that were in the top comfort category for both stinging and blurring were rated 1, those that were in the bottom comfort category for both stinging and blurring were rated 3, and those that were in the top category for either stinging or blurring but in the bottom category for the other were given the intermediate rating of 2.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A sustained release topical, aqueous ophthalmic gel suspension for dry eye applications which is administrable to the eye in drop form as a gel and which releases water and one or more ophthalmic demulcents or ophthalmic vasoconstrictors contained therein, comprising water, and from about 0.1% to about 6.5% by weight, based on the total weight of the suspension, of a lightly cross-linked carboxyl-containing polymer having a particle size of not more than about 30 μm in equivalent spherical diameter, at least about 60% by weight of the polymer having been prepared by suspension or emulsion polymerizing at least about 50% by weight of one or more carboxyl-containing monoethylenically unsaturated monomers and from about 0.01% to about 5% by weight of a non-polyalkenyl polyether difunctional cross-linking agent, the weight percentages of monomers being based on the total weight of monomers polymerized, and from about 0.01% to about 4% by weight, based on the total weight of the suspension, of at least one ophthalmic demulcent, or from about 0.01% to about 0.2% by weight, based on the total weight of the suspension, of at least one ophthalmic vasoconstrictor, or a mixture of at least one ophthalmic demulcent and at least one ophthalmic vasoconstrictor from which the above-stated ranges, the suspension being at a pH of from about 6.6 to about 8.0, and an osmolality of from about 50 to about 400 mOsM and having a viscosity of from about 500 to about 4,000 centipoises.

2. A suspension for dry eye applications as in claim 1 in which the pH is from about 6.8 to about 7.6.

3. A suspension for dry eye applications as in claim 1 in which the pH is from about 7.2 to about 7.4.

4. A suspension for dry eye applications as in claim 3 in which the lightly cross-linked carboxyl-containing polymer has a dry particle size of less than about 20 μm.

5. A suspension for dry eye applications as in claim 4 in which the polymer particles are essentially monodisperse.

6. A suspension for dry eye applications as in claim 5 in which the lightly cross-linked carboxyl-containing polymer is one prepared from at least about 90% by weight of one or more carboxyl-containing monoethylenically unsaturated monomers.

7. A suspension for dry eye applications as in claim 6 in which substantially all of the lightly cross-linked carboxyl-containing polymer is prepared by suspension or emulsion polymerizing acrylic acid and a non-polyalkenyl polyether difunctional cross-linking agent.

8. A suspension for dry eye applications as in claim 7 in which the cross-linking agent is 3,4-dihydroxyhexa-1,5-diene.

9. A suspension for dry eye applications as in claim 2 in which the osmolality is achieved using a physiologically and ophthalmologically acceptable salt in an amount of from about 0.01% to about 1% by weight, based on the total weight of the suspension.

10. A suspension for dry eye applications as in claim 9 in which the salt is sodium chloride.

11. A suspension for dry eye applications as in claim 10 in which the ophthalmic demulcent is at least one of sodium carboxymethyl-cellulose, hydroxyethylcellulose, hydroxypropylmethylcellulose, methylcellulose, dextran 70, gelatin, glycerin, polyethylene glycol 300, polyethylene glycol 400, polysorbate 80, propylene glycol, polyvinyl alcohol or polyvinylpyrrolidone.

12. A suspension for dry eye applications as in claim 10 in which the ophthalmic vasoconstrictor is at least one of ephedrine hydrochloride, naphazoline hydrochloride, phenylephrine hydrochloride or tetrahydrozoline hydrochloride.

13. A suspension for dry eye applications as in claim 12 wherein at least about 90% of the polymer particles are within a no more than about 10 μm band of major particle size distribution, and no more than about 10% of the total particles are fines.

14. A suspension for dry eye applications as in claim 13 that also contains from about 0.01 to about 0.5% by weight, based on the total weight of the suspension, of a stabilizer.

15. A suspension for dry eye applications as in claim 14 in which the stabilizer is ethylenediaminetetraacetic acid or its sodium salt, present in an amount of from about 0.025 to about 0.3% by weight, based on the total weight of the suspension.

16. A suspension for dry eye applications as in claim 15 in which the ophthalmic demulcent comprises gelatin.

17. A suspension for dry eye applications as in claim 15 in which the ophthalmic demulcent is a mixture of gelatin and hydroxyethylcellulose.

18. A suspension for dry eye applications as in claim 15 in which the ophthalmic demulcent is a mixture of gelatin and dextran.

19. A suspension for dry eye applications as in claim 15 in which the ophthalmic demulcent is a mixture of dextran and polyethylene glycol 400.

20. A sustained release topical, aqueous ophthalmic gel suspension for dry eye applications which is administrable to the eye in drop form as a gel and which releases water and one or more ophthalmic demulcents contained therein, comprising water, from about 0.1% to about 2.0% by weight, based on the total weight of the suspension, of a lightly cross-linked carboxyl-containing essentially monodisperse polymer having a dry particle size of not more than about 30 μm in equivalent spherical diameter, prepared by suspension or emulsion polymerizing acrylic acid and from about 0.01% to about 1% by weight of 3,4-hydroxyhexa-1,5-diene, the weight percentage of monomers being based on the total weight of monomers polymerized, and from about 0.01% to about 4% by weight, based on the total weight of the suspension, of at least one of gelatin, hydroxyethylcellulose, dextran and polyethylene glycol 400 as an ophthalmic demulcent, the suspension being at a pH of from about 7.2 to about 7.4 and an osmolality of from about 100 to about 300 mOsM and having a viscosity of from about 600 to about 3,000 centipoises.

21. A gel suspension for dry eye applications as in claim 20 wherein at least about 80% of the polymer particles are within a no more than about 10 μm band of major particle size distribution and no more than about 20% of the total particles are fines.

22. A gel suspension for dry eye applications as in claim 20 wherein at least about 90% of the polymer particles are within a no more than about 10 μm band of major particle size distribution and no more than about 10% of the total particles are fines.

23. A gel suspension for dry eye applications as in claim 20 wherein at least about 95% of the polymer particles are within a no more than about 10 μm band of major particle size distribution and no more than about 5% of the total particles are fines.

24. The gel suspension for dry eye applications as in claim 21 wherein the band of major particle distribution is from about 1 μm to about 5 μm.

25. A method of treating dry eye which comprises:
preparing a sustained release topical ophthalmic gel suspension, at a pH of from about 7.2 to about 7.4 and an osmolality of from about 100 to aeb out 300 mOsM and a viscosity of from about 600 to about 3,000 cps, containing water, and from about 0.1% to about 2.0% by weight based on the total weight of the suspension, of a lightly cross-linked carboxyl-containing essentially monodisperse polymer having a dry particle size of not more than about 30 μm in equivalent spherical diameter, prepared by suspension or emulsion polymerizing acrylic acid and from about 0.01% to about 1% by weight of 3,4-hydroxyhexa-1,5-diene, the weight percentages of the monomers being based on the total weight of monomers polymerized, and from about 0.01% to about 4% by weight, based on the total weight of the suspension, of an ophthalmic demulcent constituted by at least one of gelatin, hydroxyethylcellulose, dextran and polyethylene glycol 400,
administering the gel to the eye to contact the conjunctival mucosa for a time period sufficient to moisturize that contacted mucosa membrane,
wherein the gel remains in the eye to provide sustained release of both water and the demulcent.

26. The method of claim 25 wherein the gel is applied in an amount sufficient to provide about 0.025 to about 1 mg/cm² of the polymer to the mucosa of the eye.

27. A method of preparing a sustained release dry eye formulation comprising:
preparing a topical ophthalmic gel suspension, at a pH of from about 7.2 to about 7.4 and an osmolality of from about 100 to about 300 mOsM, containing water, and from about 0.1% to about 2.0% by weight based on the total weight of the suspension, of a lightly cross-linked carboxyl-containing essentially monodisperse polymer having a dry particle size of not more than about 30 μm in equivalent spherical diameter, prepared by suspension or emulsion polymerizing acrylic acid and from about 0.01% to about 1% by weight of 3,4-hydroxyhexa-1,5-diene, the weight percentages of the monomers being based on the total weight of monomers polymerized, and from about 0.01% to about 4% by weight, based on the total weight of the suspension, of an ophthalmic demulcent constituted by at least one of gelatin, hydroxyethylcellulose, dextran and polyethylene glycol 400, and
packaging the gel at a viscosity of from about 600 to about 3,000 cps, for administration to the eye in drop form.

28. A sustained release topical, aqueous ophthalmic gel suspension for dry eye applications which is administrable to the eye in drop form as a gel and which releases water and one or more ophthalmic demulcents or ophthalmic vasoconstrictors contained therein, comprising water, and from about 0.1% to about 6.5% by weight, based on the total weight of the suspension, of a lightly cross-linked carboxyl-containing polymer having a particle size of not more than about 50 μm in equivalent spherical diameter, at least about 60% by weight of the polymer having been prepared by suspension or emulsion polymerizing at least about 50% by weight of one or more carboyxl-containing monoethylenically unsaturated monomers and from about 0.01% to about 5% by weight of a cross-linking agent, the weight percentages of monomers being based on the total weight of monomers polymerized, and from about 0.01% to about 4% by weight, based on the total weight of the suspension, of at least one ophthalmic demulcent, or from about 0.01% to about 0.2% by weight, based on the total weight of the suspension, of at least one ophthalmic vasoconstrictor, or a mixture of at least one ophthalmic demulcent and at least one ophthalmic vasoconstrictor from which the above-stated ranges, the suspension being at a pH of from about 6.6 to about 8.0, and an osmolality of from about 50 to about 400 mOsM and having a viscosity of from about 500 to about 4,000 centipoise, at least about 80% of the polymer particles being within a no more than 10 μm band of major particle distribution and no more than about 20% of the total particles being fines.

29. The gel suspension for dry eye application as in claim 28 wherein the band of major particle distribution is from about 1 μm to about 6 μm.

* * * * *